(12) United States Patent
Laske et al.

(10) Patent No.: US 9,801,681 B2
(45) Date of Patent: Oct. 31, 2017

(54) CATHETERS AND METHODS FOR INTRACARDIAC ELECTRICAL MAPPING

(71) Applicant: MEDTRONIC ABLATION FRONTIERS LLC, Minneapolis, MN (US)

(72) Inventors: Timothy G. Laske, Shoreview, MN (US); Joseph Allen Knight, Kokomo, IN (US); Regina E. Groves, Dellwood, MN (US)

(73) Assignee: Medtronic Ablation Frontiers LLC, Minneapolis, MN (US)

(*) Notice: Subject to any disclaimer, the term of this patent is extended or adjusted under 35 U.S.C. 154(b) by 478 days.

(21) Appl. No.: 13/749,298

(22) Filed: Jan. 24, 2013

(65) Prior Publication Data

US 2014/0052118 A1 Feb. 20, 2014

Related U.S. Application Data

(60) Provisional application No. 61/684,380, filed on Aug. 17, 2012.

(51) Int. Cl.
  *A61B 5/04* (2006.01)
  *A61B 18/14* (2006.01)
  (Continued)

(52) U.S. Cl.
  CPC .......... *A61B 18/1492* (2013.01); *A61B 5/042* (2013.01); *A61B 5/04085* (2013.01);
  (Continued)

(58) Field of Classification Search
  CPC .................. A61B 5/06; A61B 19/5244; A61B 2018/00577; A61B 5/0452; A61B 5/6858;
  (Continued)

(56) References Cited

U.S. PATENT DOCUMENTS

| 111,618 A | 2/1871 | Devlin |
| 5,704,908 A * | 1/1998 | Hofmann .............. A61N 1/327 604/21 |

(Continued)

FOREIGN PATENT DOCUMENTS

| CN | 101766502 A | 7/2010 |
| WO | 2007024983 A2 | 3/2007 |
| WO | 2012092016 A1 | 7/2012 |

OTHER PUBLICATIONS

International Search Report and Written Opinion dated Dec. 5, 2013 for International Application Serial No. PCT/US2013/054881, International Filing Date: Aug. 14, 2013 consisting of 9 pages.

(Continued)

*Primary Examiner* — Joseph Stoklosa
*Assistant Examiner* — Brian M Antiskay
(74) *Attorney, Agent, or Firm* — Christopher & Weisberg, P.A.

(57) ABSTRACT

A method and system capable of identifying ectopic foci, rotors, or conduction pathways involved in reentrant arrhythmias within cardiac tissue, and then treating identified ectopic foci, rotors, and/or pathways with either lethal or sub-lethal temperatures. The system includes a medical device having one or more mapping elements and one or more treatment elements, and a computer programmable to identify ectopic foci and rotors based at least in part on signals received from the one or more mapping elements at one or more locations.

10 Claims, 7 Drawing Sheets

(51) Int. Cl.

| | |
|---|---|
| *A61B 18/18* | (2006.01) |
| *A61B 5/00* | (2006.01) |
| *A61B 5/0408* | (2006.01) |
| *A61B 5/042* | (2006.01) |
| *A61N 1/32* | (2006.01) |
| *A61B 18/00* | (2006.01) |
| *A61B 18/24* | (2006.01) |
| *A61B 18/02* | (2006.01) |

(52) U.S. Cl.
CPC .......... *A61B 5/6852* (2013.01); *A61B 5/6855* (2013.01); *A61B 18/24* (2013.01); *A61B 2018/00267* (2013.01); *A61B 2018/00351* (2013.01); *A61B 2018/00577* (2013.01); *A61B 2018/00613* (2013.01); *A61B 2018/00839* (2013.01); *A61B 2018/0212* (2013.01); *A61B 2018/1435* (2013.01); *A61B 2505/05* (2013.01); *A61N 1/327* (2013.01)

(58) Field of Classification Search
CPC . A61B 18/1492; A61B 5/6852; A61B 5/6853; A61B 2018/00214; A61B 2018/0022; A61N 1/36146; A61N 1/362
USPC ........ 600/372–375, 377, 380–381, 422–424, 600/508–509; 607/115, 119, 121–123, 607/131
See application file for complete search history.

(56) References Cited

U.S. PATENT DOCUMENTS

| | | | | |
|---|---|---|---|---|
| 6,522,926 | B1* | 2/2003 | Kieval | A61N 1/36117 607/2 |
| 6,738,655 | B1* | 5/2004 | Sen | A61B 5/0422 600/374 |
| 8,565,851 | B2* | 10/2013 | Lau | A61B 5/042 600/374 |
| 9,173,704 | B2* | 11/2015 | Hobbs | A61B 18/1492 |
| 9,370,311 | B2* | 6/2016 | Stewart | H05K 13/0046 |
| 2002/0111618 | A1 | 8/2002 | Stewart et al. | |
| 2006/0106375 | A1 | 5/2006 | Werneth et al. | |
| 2006/0111702 | A1 | 5/2006 | Oral et al. | |
| 2008/0194979 | A1* | 8/2008 | Madry | A61B 5/02405 600/523 |
| 2009/0287202 | A1* | 11/2009 | Ingle et al. | 606/21 |
| 2009/0318849 | A1* | 12/2009 | Hobbs | A61B 18/1492 604/20 |
| 2012/0143179 | A1 | 6/2012 | Avitall | |
| 2012/0191087 | A1* | 7/2012 | Pachon Mateos et al. | 606/34 |
| 2013/0274582 | A1* | 10/2013 | Afonso | A61B 5/0422 600/374 |

OTHER PUBLICATIONS

Notice on the First Office Action, including Search Report and Text of the First Office Action (English translation), dated May 5, 2016, Application No: 201380044110.1, 16 pages.

* cited by examiner

CATHETERS AND METHODS FOR INTRACARDIAC ELECTRICAL MAPPING

CROSS-REFERENCE TO RELATED APPLICATION

This application is related to and claims priority to U.S. Provisional Patent Application Ser. No. 61/684,380, filed Aug. 17, 2012, entitled CATHETERS FOR ROTOR MAPPING, the entirety of which is incorporated herein by reference.

STATEMENT REGARDING FEDERALLY SPONSORED RESEARCH OR DEVELOPMENT n/a

FIELD OF THE INVENTION

The present invention relates to a method and system for cardiac mapping and ablation.

BACKGROUND OF THE INVENTION

A cardiac arrhythmia is a condition in which the heart's normal rhythm is disrupted. There are many types of cardiac arrhythmias, including supraventricular arrhythmias that begin above the ventricles (such as premature atrial contractions (PACs), atrial flutter, accessory pathway tachycardias, atrial fibrillation, and AV nodal reentrant tachycardia (AVNRT)), ventricular arrhythmias that begin in the lower chambers of the heart (such as premature ventricular contractions (PVCs), ventricular tachycardia (VT), ventricular fibrillation, and long QT syndrome), and bradyarrhythmias that involve slow heart rhythms and may arise from disease in the heart's conduction system. Further, cardiac arrhythmias may be classified as reentrant or non-reentrant arrhythmias. In reentrant arrhythmias, the propagating wave of bioelectricity that normally spreads systematically throughout the four chambers of the heart instead circulates along a myocardial pathway and around an obstacle (reentry point) or circulates freely in the tissue as a scroll wave or spiral (referred to herein as "rotors"). In non-reentrant arrhythmias, propagation of the normal bioelectricity wave may be blocked or initiated at abnormal (ectopic) locations.

Certain types of cardiac arrhythmias, including ventricular tachycardia and atrial fibrillation, may be treated by ablation (for example, radiofrequency (RF) ablation, cryoablation, ultrasound ablation, laser ablation, and the like), either endocardially or epicardially. However, a physician must first locate the point of reentry, ectopic focus, or regions of abnormal conduction to effectively treat the arrhythmia. Unfortunately, locating the best site for ablation has proven to be very difficult, even for the most skilled physicians.

Cardiac electrical mapping (mapping the electrical activity of the heart that is associated with depolarization and/or repolarization of the myocardial tissues) is frequently used to locate an optimal site for ablation, for instance, a reentry point, ectopic focus, or a site of abnormal myocardium. However, the source of an arrhythmia may be difficult to determine based upon the sensed electrogram morphology. In addition to signals emanating from the local myocardium, the electrogram morphology may include fractionation due to poor electrode contact, electrode design, or complex electrical activity in the vicinity of the electrodes. The signals may also include "far-field" content from distant tissues (such as detection of ventricular activity on atrial electrodes) or the signal may be attenuated due to disease, ischemia, or tissue necrosis. Further, ablation of one or more identified sites may also be problematic. To date, such ablations require either substantial trial and error (for example, ablation of all sources of complex fractionated electrograms) or the use of separate mapping and ablation devices (complex mapping systems utilizing multielectrode arrays or baskets may be used to identify an ablation site, but cannot also be used to ablate the tissue). Therefore, a system and method are desired that not only streamline the site identification and ablation processes, but also combine mapping and ablation functionality.

SUMMARY OF THE INVENTION

The system and method of the present application provides a non-ambiguous representation of the electrical activity of the myocardium at each particular site within or on the heart, improved means for searching for and testing potential ablation sites including both ectopic foci and rotors, and both mapping and treatment functionality. The non-ambiguous representation of local myocardial depolarization, repolarization timing, and action potential duration is enabled through the use of electrodes that are able to record local monophasic action potentials (MAPs).

The system may generally include a medical device defining a distal end including a plurality of mapping elements and a treatment element, and a control unit in communication with the medical device and programmable to identify a source of electrical conduction of interest within cardiac tissue based at least in part on signals received from the plurality of mapping elements at one or more tissue locations and programmable to treat the source of electrical conduction of interest by activating the treatment element. The treatment element may be an expandable element, such as a balloon defining an anterior face, the plurality of mapping elements being affixed to the anterior face of the balloon. The plurality of mapping elements may be arranged in a radially symmetrical pattern. Further, the balloon may have a substantially concentric spiral configuration when expanded. Alternatively, the distal end of the device may include one or more array arms, and each of which may include a first portion and a second portion, the first portion being in a plane that is substantially orthogonal to the longitudinal axis of the device. The one or more tissue areas are composed of cells, and the plurality of mapping elements may selectively transmit energy capable of ablation and/or electroporation of the cells. Further, the treatment element may selectively transmit energy capable of adjusting the temperature of the one or more tissue areas to a sub-lethal temperature, ablating the one or more tissue areas, and/or electroporating the cells of the one or more tissue areas. The device may further comprise a plurality of treatment elements, with each treatment element selectively transmitting energy capable of ablation and/or electroporation of cells. Each of the plurality of mapping elements may record monophasic action potentials, such that at least one of depolarization timing, repolarization timing, action potential morphology, and action potential duration is unambiguously determined.

The method of locating and treating a source of electrical conduction within cardiac tissue may generally include the following steps: (a) positioning one or more mapping elements affixed to a distal end of medical device in contact with cardiac tissue at a first position, the medical device being in communication with a control system including a computer having a display and programmable to execute algorithms, the cardiac tissue being composed of cells; (b) executing computer algorithms to determine directional and morphological features of the electrical conduction of interest based at least in part on signals received by the computer from the one or more mapping elements at the first position; (c) displaying on the computer display a suggested second position at which the one or more mapping elements should be placed in contact with the cardiac tissue; (d) repositioning the one or more mapping elements at the second position; (e) executing computer algorithms to determine directional and morphological features of the electrical conduction of interest based at least in part on signals received by the computer from the one or more mapping elements at the second position; (f) repeating steps (a)-(e) until a source or pathway of the electrical conduction of interest is located; and (g) activating one or more treatment elements in contact with the cardiac tissue cells to treat the cells at a non-lethal temperature and disrupt the source or pathway of the electrical conduction of interest. Treating the cells may include cooling or heating the cardiac cells at the source or pathway of electrical conduction of interest to a non-lethal temperature. The method may further include treating the cardiac cells at the source or pathway of the electrical conduction of interest at a lethal temperature, which may include cryoablation, tissue cooling, applying radiofrequency energy, applying laser energy, applying microwave energy, applying laser energy, and/or applying ultrasound energy. Additionally or alternatively, the method may further include electroporating the cardiac cells at source or pathway of the electrical conduction of interest with pulses of high voltage energy. Electroporation may be followed by delivering to the cardiac cells at the source or pathway of the electrical conduction of interest genes, proteins, drug therapy substances, agents that modify the behavior of the cells, and combinations thereof. The cardiac cells at the source or pathway of the electrical conduction of interest may be treated at a lethal temperature only after treating the cardiac cells at the source or pathway of the electrical conduction of interest at a non-lethal temperature. Furthermore, treating the cardiac cells at the source or pathway of electrical conduction of interest at a lethal temperature may terminate the electrical conduction of interest.

Alternatively, the method may include: (a) positioning one or more mapping elements affixed to a distal end of a medical device in contact with cardiac tissue at a first position, the medical device being in communication with a control system including a computer having a display, the cardiac tissue being composed of cells; (b) executing computer algorithms to determine directional and morphological features of the electrical conduction of interest based at least in part on signals received by the computer from the one or more mapping elements at the first position; (c) displaying on the computer display a suggested second position at which the one or more mapping elements should be placed in contact with the cardiac tissue; (d) repositioning the one or more mapping elements at the second position; (e) executing computer algorithms to determine directional and morphological features of the electrical conduction of interest based at least in part on signals received by the computer from the one or more mapping elements at the second position; (f) repeating steps (a)-(e) until a the source of the electrical conduction of interest is located; (g) activating one or more treatment elements in contact with the cardiac tissue cells to treat the cells at a non-lethal temperature; and (h) if (g) disrupts the source or pathway of the electrical conduction of interest, activating the one or more treatment elements in contact with the cardiac tissue cells to perform at least one of treating the cells with a lethal temperature and electroporating the cells.

The present invention advantageously provides a method and system for, with a single device, obtaining a non-ambiguous representation of depolarization and repolarization at each particular site within or on the heart, searching for and testing potential ablation sites that include ectopic foci, rotors, or conduction pathways involved in reentrant arrhythmias and ablating identified ectopic foci, rotors, and/or pathways.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
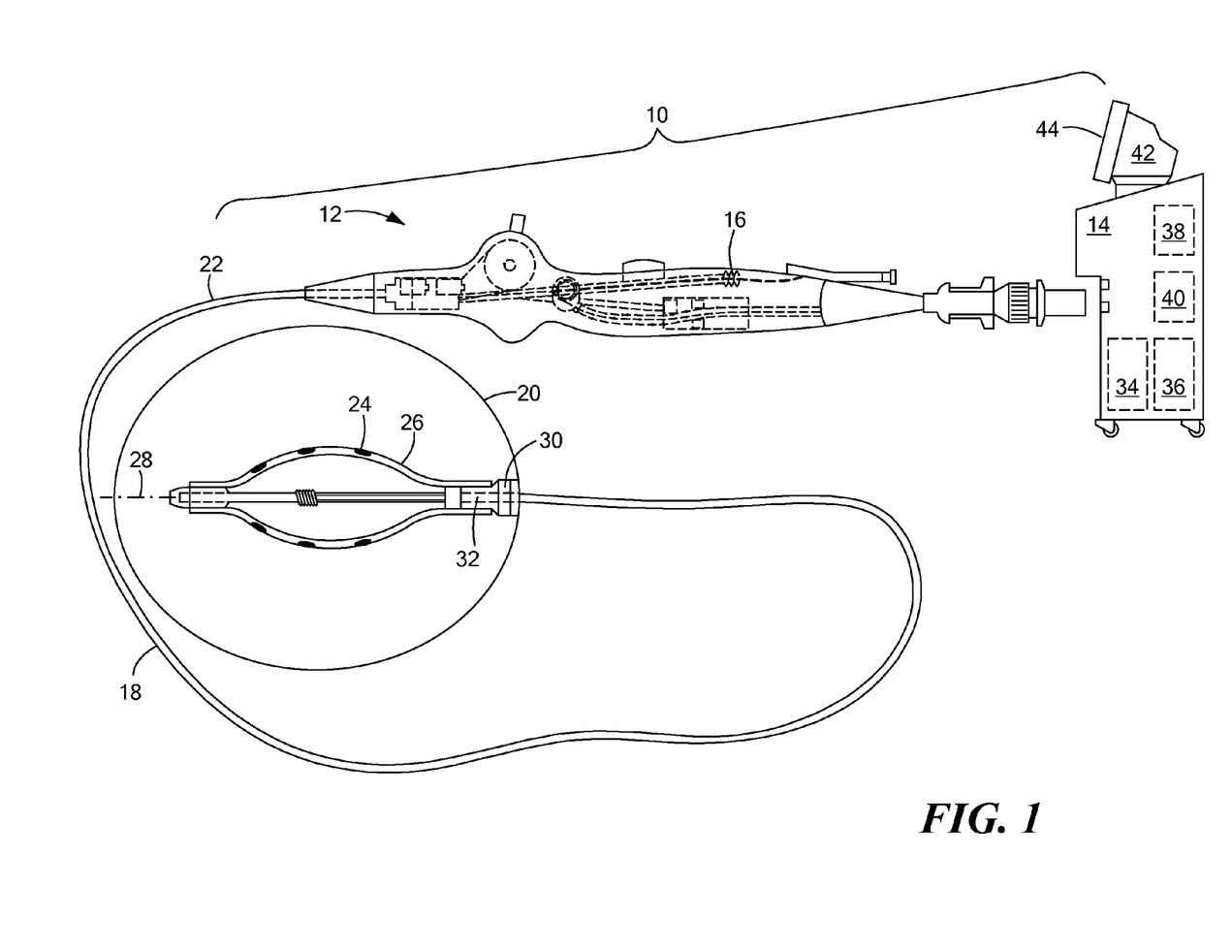
FIG. 1 shows a system in accordance with the present invention.

Now referring to FIG. 1, a system 10 in accordance with the present invention is shown. The system 10 generally includes a medical device 12 for mapping and/or treating an area of tissue and a console 14 that houses various system 10 controls. The system 10 may be adapted for radiofrequency (RF) ablation and/or phased radiofrequency (PRF) ablation, cryoablation, ultrasound ablation, laser ablation, microwave ablation, or other ablation methods or combinations thereof.

Figure 7:
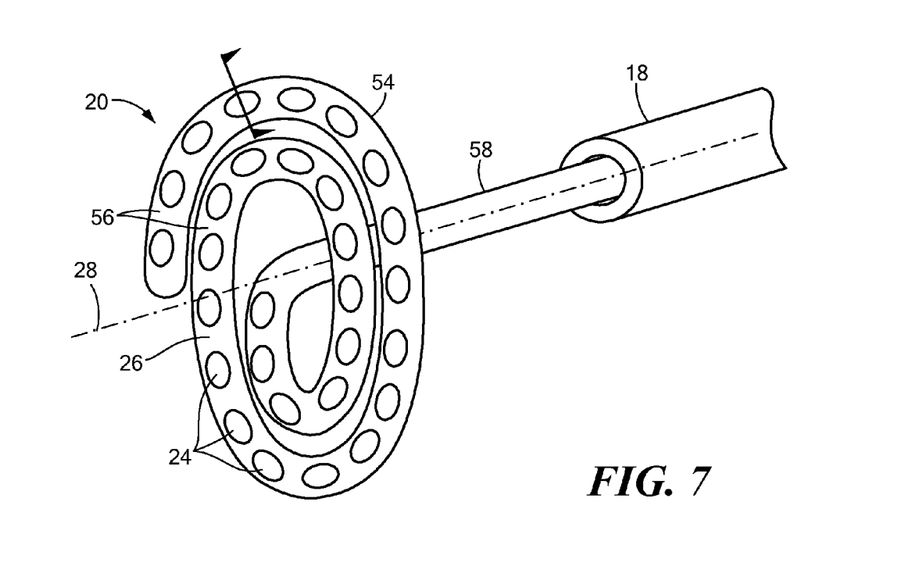
FIG. 7 shows a first embodiment of a distal end of a medical device with mapping and treatment functionality.
Figure 8:
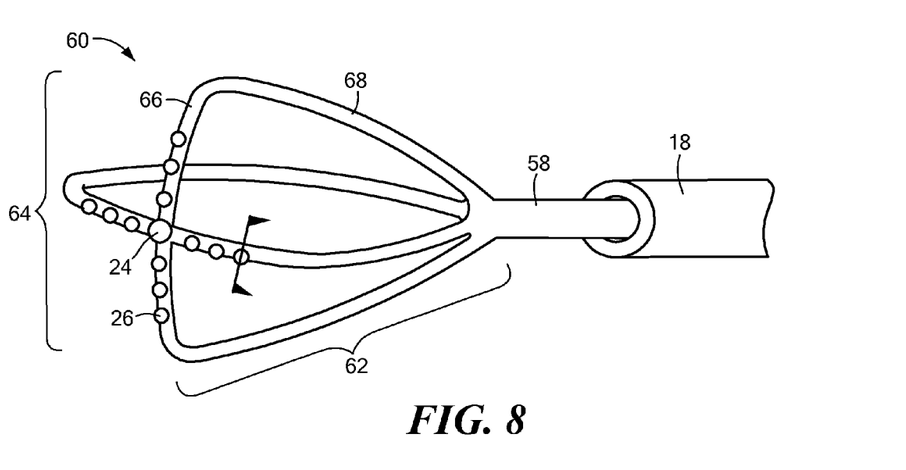
FIG. 8 shows a second embodiment of a distal end of a medical device with mapping and treatment functionality.
Figure 9:
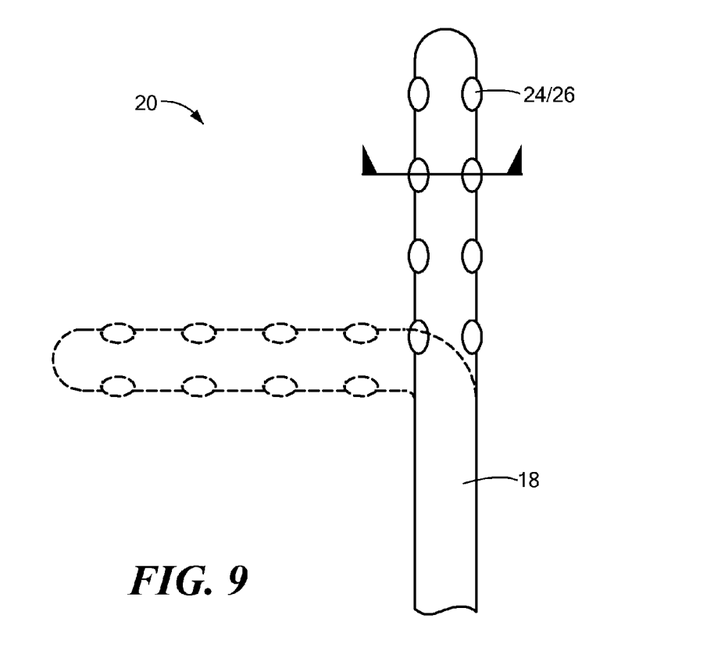
FIG. 9 shows a third embodiment of a distal end of a medical device with mapping and treatment functionality.

The device 12 may be a catheter with mapping and treatment functionality generally including a handle 16, an elongate body 18 having a distal portion 20 and a proximal portion 22, one or more mapping elements or sensors 24, and one or more treatment elements 26. The device 12 may have a longitudinal axis 28. The distal portion 20 of the device 12 may include an expandable element (such as a balloon or wire mesh), a deformable coil or concentric spiral (as shown in FIG. 7), or other array on which mapping 24 and treatment elements 26 may be disposed (for example, as shown in FIG. 8). Alternatively, the distal portion 20 of device 12 may be straight, such as a focal catheter that may be bendable to an approximately 90-degree angle (as shown in FIG. 9). The mapping 24 elements may be sensors or electrodes capable of sensing electrical activity within the myocardial cells as the cells polarize and depolarize, such as monophasic action potential (MAP) electrodes. The device 12 may also include one or more reference electrodes 30. The treatment elements 26 may be electrodes capable of transmitting thermal energy, and may be larger (that is, have more surface area) than the mapping 24 electrodes. Additionally or alternatively, the treatment elements 26 may include an expandable treatment element 26 such as a cryoballoon. Further, the device 12 may include one or more thermoelectric cooling elements.

The elongate body 18 of the device 12 may include one or more lumens 32. If the device 12 is a cryoablation catheter, for example, the elongate body 18 may include a main lumen, a fluid injection lumen in fluid communication with the coolant reservoir 34, and a fluid return lumen in fluid communication with the coolant return reservoir 36. In some embodiments, one or more other lumens may be disposed within the main lumen, and/or the main lumen may function as the fluid injection lumen or the fluid return lumen. If the ablation catheter includes thermoelectric cooling elements or electrodes capable of transmitting radiofrequency (RF), ultrasound, microwave, electroporation energy, or the like, the elongate body 18 may include a lumen in electrical communication with an energy generator 38 and/or a power source 40.

Figure 5:
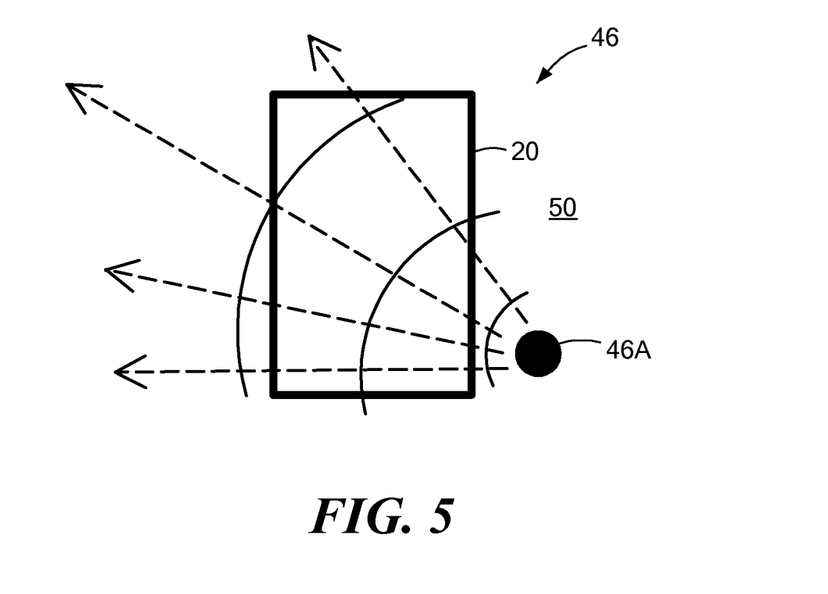
FIG. 5 shows a stylized representation of a distal end of a medical device placed a distance from an ectopic focus.
Figure 6:
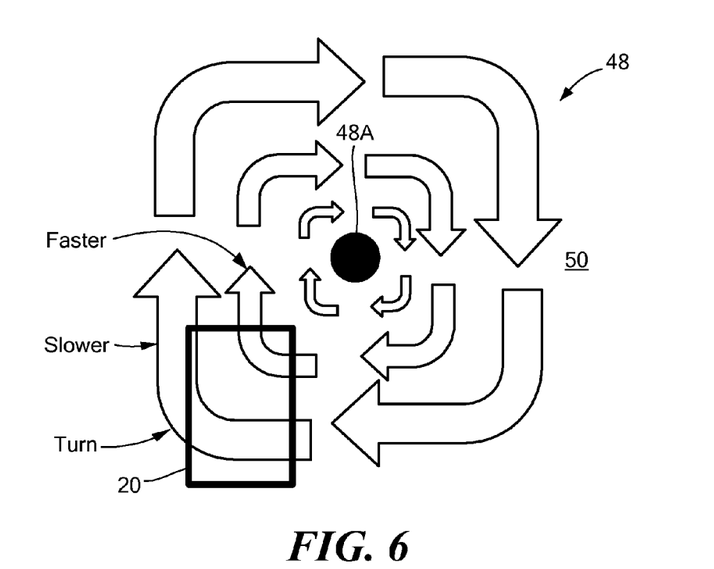
FIG. 6 shows a stylized representation of a distal end of a medical device placed a distance from a rotor.

The console 14 may be in electrical and fluid communication with the medical device 12 and include one or more fluid (such as coolant or saline) reservoirs 34, fluid return reservoirs 36, energy generators 38 (for example, an RF or electroporation energy generator), and computers 42 with displays 44, and may further include various other displays, screens, user input controls, keyboards, buttons, valves, conduits, connectors, power sources, and computers for adjusting and monitoring system 10 parameters. The computer 42 may be in electrical communication with the one or more mapping elements 24 and/or the one or more treatment elements 26 and programmable to execute an algorithm for locating one or more optimal treatment areas. For example, the computer may assess arrhythmia morphology and directionality using activation timing signals from the one or more mapping elements 24. Based on the calculated morphology and directionality, the computer may then determine one or more optimal treatment sites (for example, as shown in FIGS. 5 and 6) and communicate those sites, via one or more displays or screens, to the user.

Once an optimal treatment site is located, and the medical device 12 positioned in contact with this site, the one or more treatment elements 26 may be activated to treat the site. As a non-limiting example, the system 10 may be configured for use in cryoablation procedures. For example, the device 12 may include a cryoballoon as the treatment element 26. Once an optimal treatment site is located, the medical device 12 may be placed in contact with the treatment site and the treatment element 26 activated to cool the treatment site to a sub-lethal temperature (or heated to a sub-lethal temperature, if non-cryogenic energy modalities are used). If the application of the sub-lethal temperature abates, disrupts, or temporarily terminates the arrhythmia, the user may then choose to increase the cooling effect, or lower the temperature, of the one or more treatment elements 26 in order to permanently ablate the tissue of the treatment site (or raise the temperature to a lethal temperature, if non-cryogenic energy modalities are used). Thus, alternatively, the user may choose to ablate the treatment site once it has been located and confirmed as an accurate target. Additionally or alternatively, once an optimal treatment site is located, the medical device 12 may be placed in contact with the treatment site and activated to transmit short pulses of high voltage in order to electroporate the cells of the treatment site. This electroporation may be used to disable cells, ablate cells, or prepare cells for subsequent therapies such as gene delivery, protein delivery, or other therapeutic agent or substance intended to modify the behavior of the cells.

Figure 2:
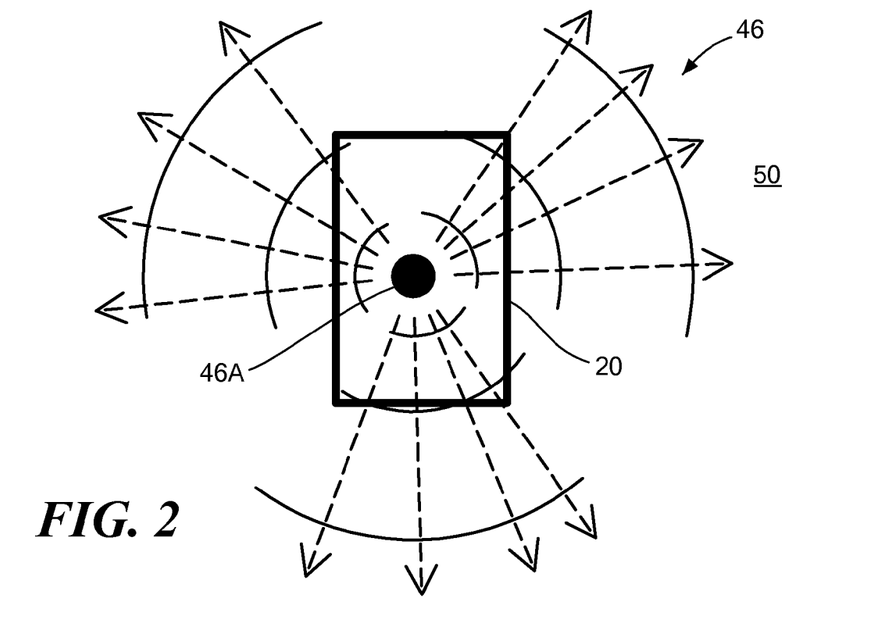
FIG. 2 shows a stylized representation of a distal end of a medical device placed substantially centered on an ectopic focus.
Figure 3:
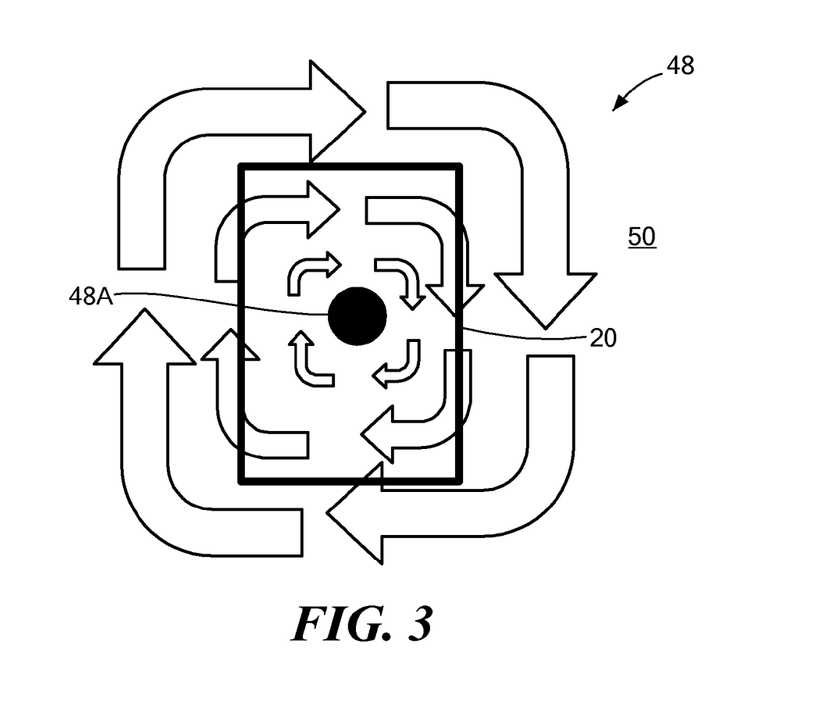
FIG. 3 shows a stylized representation of a distal end of a medical device placed substantially centered on a rotor.
Figure 4:
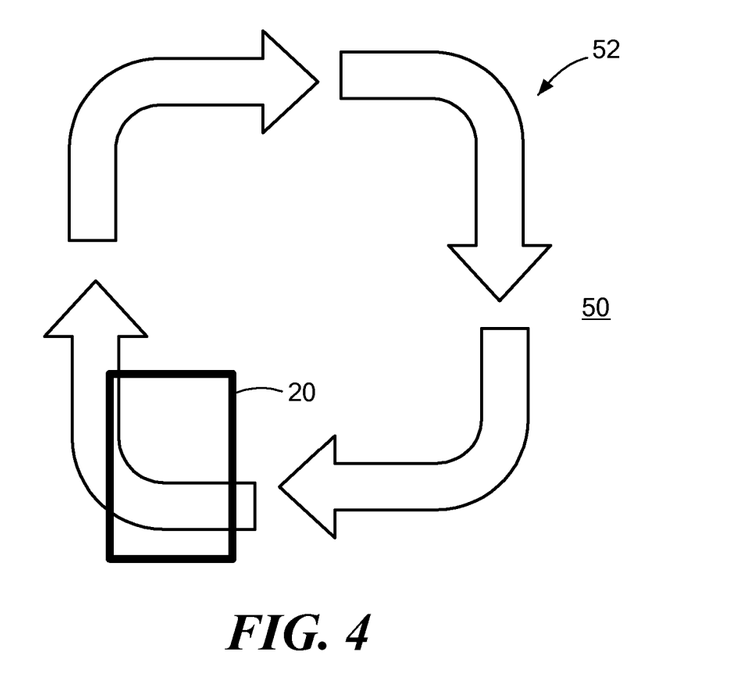
FIG. 4 shows a stylized representation of a distal end of a medical device placed substantially on a reentrant pathway.

Now referring to FIGS. 2 and 3, stylized representations of a distal portion 20 of a medical device 12 (depicted as a rectangle) placed substantially centered on an ectopic focus and a rotor are shown, respectively, on cardiac tissue 50. In FIG. 2, the small black circle represents the center of the focus 46A. Likewise, in FIG. 3, the small black circle represents the position of rotation of the rotor 48A (which, for simplicity, will be referred to as the "center" 48A of the rotor 48). Referring to FIG. 4, a stylized representation of a distal portion 20 of a medical device 12 placed substantially within a reentrant pathway 52 is shown. The stylized distal portion 20 shown in FIGS. 2-4 may represent any configuration, such as a coil or concentric spiral (for example, as shown in FIG. 7), a crossed-arm array (for example, as shown in FIG. 8), or a linear distal portion 20 (for example, as shown in FIG. 9). For simplicity, the distal portion 20 is depicted as a rectangle in FIGS. 2-4.

In FIG. 2, a small black circle is shown within the rectangle, representing a distal portion 20 of a medical device 12 being substantially centered above the center 46A of an ectopic focus 46. The dashed arrows represent propagating waves of bioelectricity emanating from the center 46A of the ectopic focus 46 in an outward direction through cardiac tissue 50. In FIG. 3, a small black circle is shown within the rectangle, representing a distal portion 20 of a medical device 12 being substantially centered above the center 48A of the rotor 48. The arrows represent a pattern of propagating waves of bioelectricity from the center (position of rotation 48A), with smaller arrows representing a higher frequency and larger arrows representing a lower frequency. The direction of the arrow indicates the direction of the wave. In FIG. 4, the rectangle represents the distal portion 20 of a medical device 12 being positioned substantially on a reentrant loop 52. The pattern of propagating waves in the rotor 48 may be a spiral, scroll wave, or other nonlinear pattern, and the location of the center 48A of the rotor may change. The propagating waves may move outward from the center 46A of an ectopic focus 46 in any direction or in any pattern away from the center 48A in a rotor 48. For reentrant loops 52, the electrical conduction may be in a repeating circuit with or without the involvement of the tissue in the center of the circuit. In contrast, a rotor 48 (or spiral wave reentry) may involve the center 48A of the circuit, and the circuit can be continuously varying and not following a uniquely defined pathway. For rotors 48 and ectopic foci 46, the frequency of a wave will generally decrease as it moves farther from the center of the ectopic focus 46A or rotor center 48A. That is, a mapping element 24 positioned proximal the center 46A of an ectopic focus 46 or rotor center 48A will record a greater depolarization frequency than a mapping element 24 positioned a greater distance from the center 46A of the ectopic focus 46 or rotor center 48A. Further, the one or more mapping elements 24 may each record a direction of a curved propagating wave, which data is used by the computer 42 to calculate the rotor pattern. For reentrant loops 52, the circuit may define a discrete pathway having a width. Particularly if the width is narrow, small relocations of the device distal portion 20 may detect the pathway, which will have a frequency that is independent of neighboring tissue. An optimal ablation site for a reentrant loop 52 is anywhere within the loop 52 that will disrupt the conduction loop or pathway. Thus, FIG. 4 the center of the reentrant loop 52 is not represented by a small black circle as in FIGS. 2 and 3, because the center of the reentrant loop 52 may not be the optimal ablation site.

Now referring to FIGS. 5 and 6, stylized representation of a distal portion 20 of a medical device 12 (depicted as a rectangle) placed a distance from the center 46A of an ectopic focus 46 and a rotor center 48A are shown, respectively. The representations in FIGS. 5 and 6 (such as arrows, rectangles, and black circles) are the same as in FIGS. 2-4. The propagating waves may move outward from the center 46A of the ectopic focus 46 in any direction or in any pattern away from the central point in a rotor, but the frequency of a wave will generally decrease as it moves farther from the center 46A of the ectopic focus 46 or rotor center 48A. Using the morphological and directional characteristics of one or more propagating waves sensed by the one or more mapping elements 24 and communicated to the computer 42, the computer 42 may communicate to the user (via one or more screens or other displays 44) suggested treatment sites, or at a minimum a general distance and direction that might allow the user to move closer to the origin of the ectopic focus 46 or rotor 48. Using the algorithm discussed above, the computer 42 may continue to suggest treatment sites until an optimal treatment site, a site substantially at the center 46A of an ectopic focus 46, rotor center 48A, or reentrant loop 52, is located.

Figure 11:
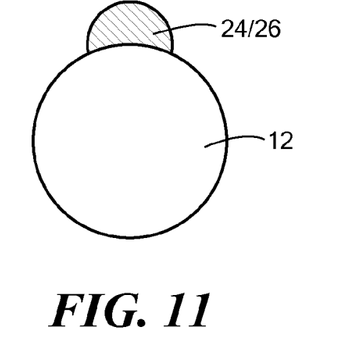
FIG. 11 shows a cross section of a first embodiment of a mapping element such as in FIG. 7, 8, or 9.
Figure 12:
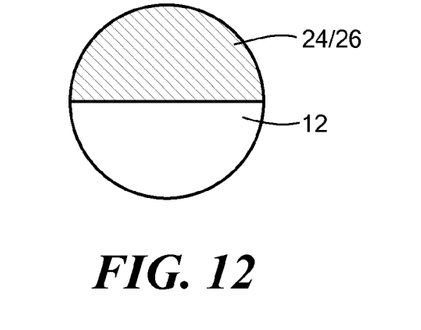
FIG. 12 shows a cross section of a second embodiment of a mapping element such as in FIG. 7, 8, or 9.

Now referring to FIG. 7, a first embodiment of a distal portion 20 of a medical device 12 with mapping and ablation functionality is shown. The distal portion 20 may have a coil or concentric spiral configuration 54 with a plurality of turns. The coil or concentric spiral 54 may lie in a plane that is substantially orthogonal to the longitudinal axis 28 of the device 12. Each turn includes an anterior face 56, on which is positioned one or more mapping elements 24 and/or one or more treatment elements 26. If the spiral 54 is the treatment element 26, then the face 56 of the spiral 54 may only contain mapping elements 24. To enhance surface area and tissue contact, the one or more mapping 24 and/or treatment elements 26 may have a curved or semi-circular profile that extends from the anterior face 56 of each turn of the spiral 54 (for example, as shown in FIG. 11). As a non-limiting example, as shown in FIG. 7, the spiral 54 is the treatment element 26 on which a plurality of mapping elements 24 are borne. The mapping elements 24 may have a curved or semi-circular profile that extends from the anterior face 56 of each turn of the spiral 54. Alternatively, the one or more mapping 24 and/or treatment elements 26 may be set within and flush with the anterior face 56 of each turn (for example, as shown in FIG. 12). The distal portion 20 may be affixed to a shaft 58 that is slidably movable within the elongate body 18 of the device 12, or the distal portion 20 may be continuous with the elongate body 18 of the device 12. For example, the distal portion 20 may include a cryoballoon coupled to the elongate body 18 that may be inflated with coolant to assume the coiled configuration shown in FIG. 7. Alternatively, the distal portion 20 may be composed of a resilient and deformable material, and may assume a first position for allowing passage through the vasculature to the region of interest and a second extended position for mapping and/or treatment. Further, the resilient and deformable material may be biased toward either the first or second position and may be steerable by one or more pull wires, guide wires, rods, or other steering mechanisms controllable at or proximal to the handle 16 of the device 12. Similarly, the distal portion 20 may be an elongated cryoablation element that can assume a coiled configuration. For example, the distal portion 20 may include an inflatable element or balloon that, when inflated, assumes the coiled configuration. Further, the balloon may bear one or more mapping 24 and/or treatment 26 elements on an outer surface (used, for example, for RF ablation, microwave ablation, ultrasound ablation, electroporation, or other treatment method), or may enclose a coolant so the balloon may be used to cool and/or ablate a target tissue area. The one or more treatment elements 26 may be in fluid communication with a coolant reservoir 34 and/or may be cooled using a thermoelectric cooler or cryogenic fluid. Additionally or alternatively, the one or more treatment elements 26 may be capable of transmitting RF, laser, ultrasound, or microwave energy, or the like.

Figure 10:
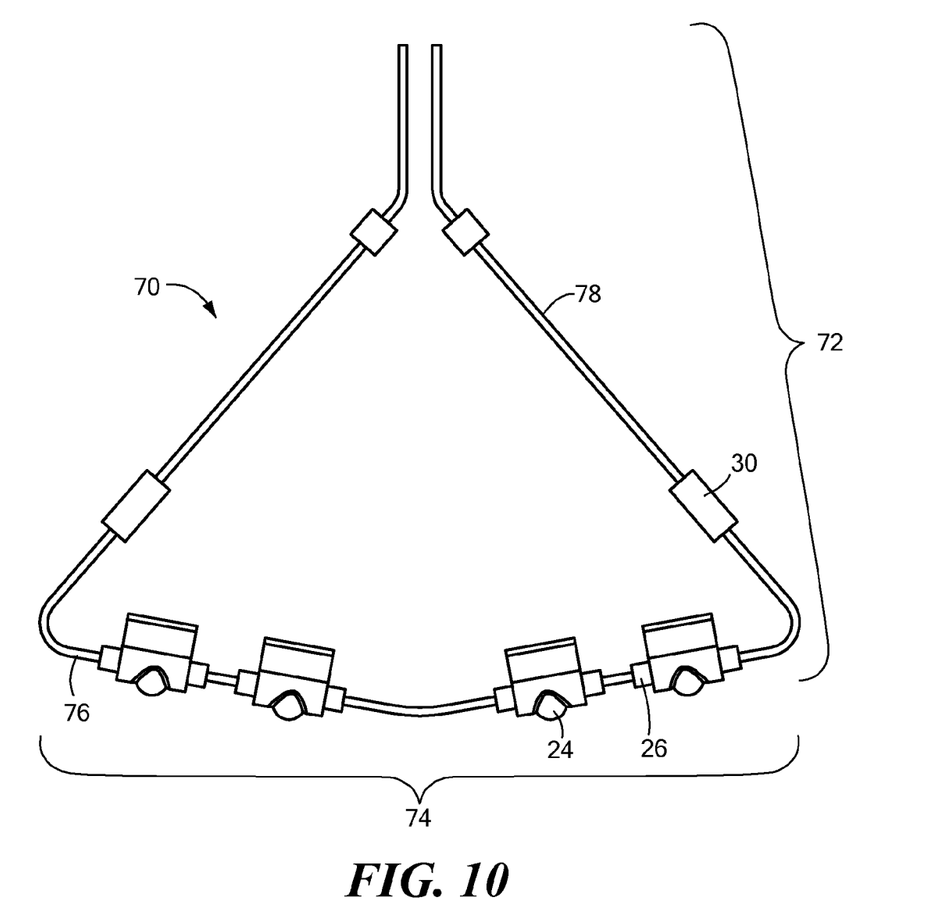
FIG. 10 shows a fourth embodiment of a distal end of a medical device with mapping and treatment functionality.

Now referring to FIG. 8, a second embodiment of a distal portion 20 of a medical device 12 with mapping 24 and ablation functionality is shown. The distal portion 20 may include a crossed-arm array 60 that includes a plurality of arms 62, each of which bearing one or more mapping 24 and/or treatment elements 26 at an anterior face 64 of the array 60. Each arm 62 may include a first portion 66 at the anterior face 64 of the array 60 on which the one or more mapping 24 and/or treatment elements 26 are borne, and a second portion 68 that is coupled to the device 12. Each electrode may serve a mapping and/or ablation function, and it is conceived that mapping elements 24 may protrude from underlying ablative structures (as shown and described in FIGS. 11 and 13). The point at which the first 66 and second 68 portion of each arm 62 meet may form an acute angle. The second portion 68 of each arm 62 may be affixed to a shaft 58 that is slidably movable within the elongate body 18 of the device 12, or affixed directly to the elongate body 18. To enhance surface area and tissue contact, the one or more mapping 24 and/or treatment elements 26 may have a curved or semi-circular profile that extends from the first portion 66 of each arm 62 (for example, as shown in FIG. 10). Alternatively, the one or more mapping 24 and/or treatment elements 26 may be set within and flush with the first portion 66 of each arm 62 (for example, as shown in FIG. 11). Each element may be capable of both mapping and ablation. Alternatively, for example, the mapping element 24 may protrude farther from the center point 69 of the cross-arm array 60 to enhance tissue contact and signal quality, whereas the treatment elements 26 may cover a larger "footprint" for ablation of larger areas of tissue. Further, the distal portion 20 may be composed of a resilient and deformable material, and may assume a first position for delivery (not shown) and a second position for mapping and/or treatment (as shown in FIG. 8). When in the second expanded position, the first portion 66 of each arm 62 may lie in a plane that is substantially orthogonal to the longitudinal axis 28 of the device 12. Still further, the resilient and deformable material may be biased toward either the first or second position and may be steerable by one or more pull wires, guide wires, rods, or other steering mechanisms controllable at or proximal to the handle 16 of the device 12. The one or more treatment elements 26 may be in fluid communication with a coolant reservoir 34 and/or may be cooled using a thermoelectric cooler or cryogenic fluid. Alternatively, the one or more treatment elements 26 may be capable of transmitting RF, laser, ultrasound, microwave, electroporation energy, or the like.

Now referring to FIG. 9, a third embodiment of a distal portion 20 of a medical device 12 with mapping and ablation functionality is shown. The device 12 may be a focal catheter or similar device, without a distal array or configuration and the one or more mapping 24 and/or treatment elements 26 (referred to in FIG. 9 as "24/26") being borne along the distal portion 20 of the elongate body 18. Alternatively, the distal portion 20 of the device 12 may be composed of a material different than that of the elongate body 18, may have a different diameter or rigidity, or the like. To enhance surface area and tissue contact, the one or more mapping 24 and/or treatment elements 26 may have a curved or semi-circular profile that extends from the distal portion 20 (for example, as shown in FIG. 10). Alternatively, the one or more mapping 24 and/or treatment elements 26 may be set within and flush with the distal portion 20 (for example, as shown in FIG. 11). Additionally, the distal portion 20 may be composed of a resilient and deformable material that permits bending of the distal portion 20, such as into a right-angle (or other acute or obtuse angle) bend, as depicted in dashed lines in FIG. 9. The one or more mapping 24 and/or treatment elements 26 may be disposed longitudinally along the distal portion 20. The one or more treatment elements 26 may be in fluid communication with a coolant reservoir and/or may be cooled using a thermoelectric cooler or cryogenic fluid. Additionally or alternatively, the one or more treatment elements 26 may be capable of transmitting RF, laser, ultrasound, microwave, electroporation energy, or the like. When mapping cardiac tissue, the distal portion 20 may either be oriented or bent to position one or more mapping elements 24 in contact with the tissue (for example, in a linear pattern). When treating cardiac tissue (either with lethal or sub-lethal temperatures), the device 12 may be used like a focal catheter to create a substantially circular focal lesion (such as when only the distal tip is placed in contact with the treatment site) or bent to create a substantially linear lesion (such as when a longitudinal surface of the distal portion 20 including two or more treatment elements 26 is placed in contact with the treatment site).

Now referring to FIG. 10, a fourth embodiment of a distal portion 20 of a medical device 12 with mapping and ablation functionality is shown. The distal portion 20 may include an array 70 that includes one or more arms 72 bearing one or more mapping 24 and/or treatment elements 26. Each arm 72 may include a first portion 76 at the anterior face 74 of the array 70 on which the one or more mapping 24 and/or treatment elements 26 are borne, and a second portion 78 that is coupled to the device 12. The array 70 may further include one or more reference electrodes 30. As shown in FIG. 10, the one or more treatment elements 26 may each include a mapping element 24, which may protrude from the corresponding treatment element 26. The point at which the first 76 and second 78 portion of each arm 72 meet may form an acute angle. The second portion 78 of each arm 72 may be affixed to a shaft 58 that is slidably movable within the elongate body 18 of the device 12, or affixed directly to the elongate body 18. The cross-section of each treatment element 26/mapping element 28 combination may be as shown in detail in FIG. 13. Further, the distal portion 20 may be composed of a resilient and deformable material, and may assume a first position for delivery (not shown) and a second position for mapping and/or treatment (as shown in FIG. 10). When in the second expanded position, the first portion 76 of each arm 72 may lie in a plane that is substantially orthogonal to the longitudinal axis 28 of the device 12. Still further, the resilient and deformable material may be biased toward either the first or second position and may be steerable by one or more pull wires, guide wires, rods, or other steering mechanisms controllable at or proximal to the handle 16 of the device 12. The one or more treatment elements 26 may be in fluid communication with a coolant reservoir 34 and/or may be cooled using a thermoelectric cooler or cryogenic fluid. Additionally or alternatively, the one or more treatment elements 26 may be capable of transmitting RF, laser, ultrasound, or microwave energy, or the like.

Now referring to FIGS. 11 and 12, cross sections of a first embodiment and a second embodiment of a mapping element 24 such as in FIGS. 7, 8, and 9 are shown. The cross section is taken along line A-A of FIGS. 7-9. As described above, the one or more mapping 24 and/or treatment elements 26 (referred to as "24/26" in FIGS. 11 and 12) may have a curved or semi-circular profile that protrudes from the device 12 or portion thereof (for example, array arm, elongate body, or the like) in order to enhance surface area and tissue contact (as shown in FIG. 11). Alternatively, the one or more mapping 24 and/or treatment elements 26 may be set within and flush with the device 12 (as shown in FIG. 12).

Figure 13:
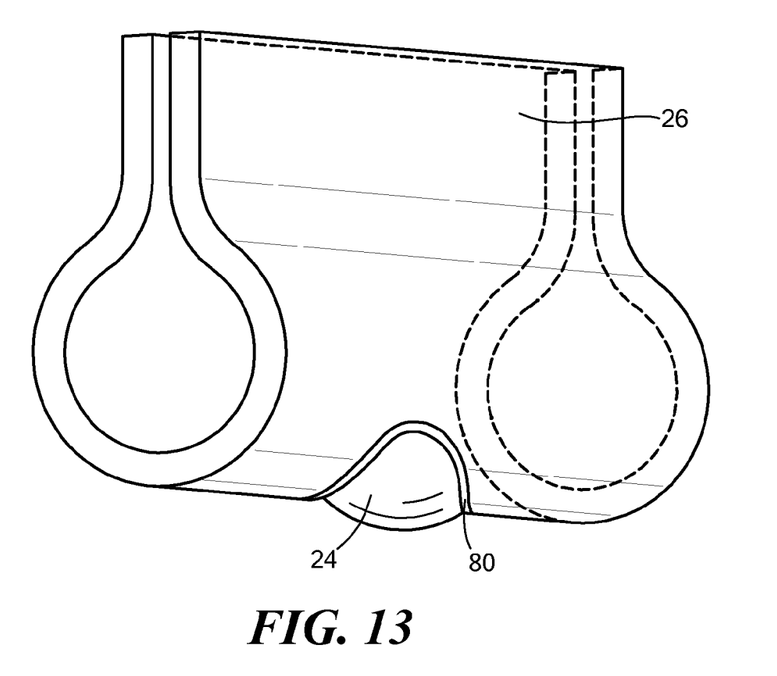
FIG. 13 shows a perspective view of a third embodiment of a mapping element such as in FIG. 10.

Now referring to FIG. 13, a perspective view of a third embodiment of a mapping element 24 such as in FIG. 10 is shown. The one or more treatment elements 26 may each include a mapping element 24 protruding therefrom. Further, an insulative layer 80 may be included that surrounds each mapping element 24 to electrically isolate it relative to the treatment element 26 and thus reduce the region of tissue from which electrical activity is sensed. The insulative layer 80 may also act to at least partially shield the one or more mapping elements 24 from energy transmitted by the one or more treatment elements 26.

Figure 14:
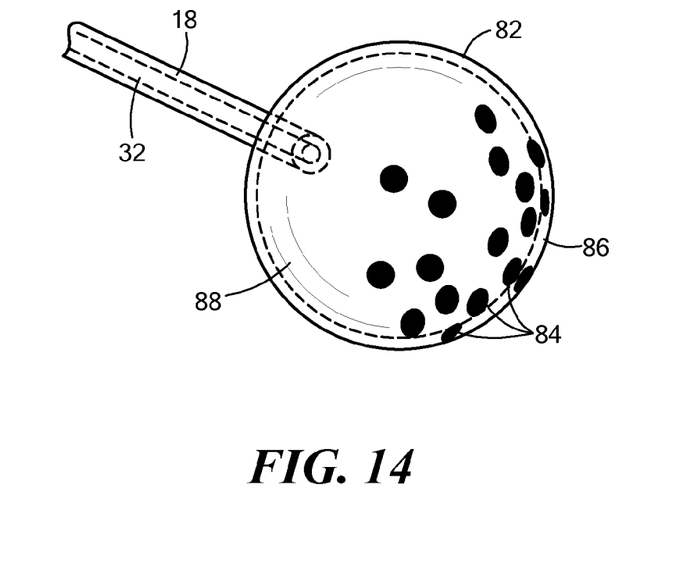
FIG. 14 shows a fifth embodiment of a distal end of a medical device with mapping and treatment functionality.

Now referring to FIG. 14, a fifth embodiment of a distal portion 20 of a medical device 12 with mapping and ablation functionality is shown. The distal portion 20 may include an inflatable element or balloon 82 on which a plurality of electrodes 84 are borne. For example, the electrodes 84 may be small button electrodes that are affixed to the outer surface of the balloon 82. The electrodes 84 may be affixed to an anterior face 86 of the balloon 82, and they may be affixed in a radially symmetrical pattern. The electrodes 84 may be used to map and ablate an area of target tissue. Additionally or alternatively, the electrodes 84 may be used to map tissue, whereas ablation of the tissue is accomplished through the use of a coolant that is circulated within the balloon lumen 88.

It will be understood that any of the above devices may be used to apply electroporation energy to the cells of the area of target tissue. Electroporation utilizes high electric field amplitude electrical pulses to effectuate a physiological modification (i.e. permeabilization) of the cells to which the energy is applied. Such pulses may preferably be short (for example, having a nanosecond, microsecond, or millisecond pulse width) in order to allow application of high voltage without a large flow of electrical current that would result in significant tissue heating. In particular, the pulsed energy induces the formation of microscopic pores or openings in the cell membrane. Depending on the characteristics of the electroporation pulses, an electroporated cell can survive electroporation (referred to as "reversible electroporation")

or be killed by electroporation (referred to as "irreversible electroporation" or "IEP"). Reversible electroporation may be used to transfer agents, including large molecules, into targeted cells for various purposes. Thus, electroporation may be used to disable tissue cells, ablate tissue cells, or prepare tissue cells for subsequent therapies, such as gene delivery, protein delivery, or delivery of other therapeutic agents or substances intended to modify the behavior of the target tissue cells.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical system comprising: a medical device defining a distal end including at least one array arm a plurality of treatment elements coupled to the at least one array arm, each treatment element having a mapping element protruding therefrom, at least a portion of each mapping element having an insulative layer that electrically isolates the mapping element from the treatment element; and a control unit in communication with the medical device, the control unit being configured to deliver electroporation energy to the plurality of electroporation treatment elements and being programmed to: assess a morphology of an electrical conduction of interest within cardiac tissue based on monophasic action potential signals received from the mapping elements; assess a directionality of the electrical conduction of interest based on signals received from the mapping elements; identify a source of the electrical conduction of interest based on the morphology and directionality of the electrical conduction of interest; determine and communicate to a user one or more optimal treatment sites; and disrupt the electrical conduction of interest by activating the plurality of treatment elements in at least one of the one or more optimal treatment sites, activating the plurality of treatment elements including delivering electroporation energy from the control unit to the plurality of electroporation treatment elements.

2. The system of claim 1, wherein the plurality of mapping elements are arranged in a radially symmetrical pattern.

3. The system of claim 1, wherein the one or more tissue areas are composed of cells and wherein the plurality of mapping elements selectively transmit energy capable of at least one of ablation and electroporation of the cells.

4. The system of claim 1, wherein the one or more tissue areas are composed of cells and wherein the treatment element is configured to additionally transmit energy capable of at least one of adjusting the temperature of the one or more tissue areas to a sub-lethal temperature and ablating the one or more tissue areas.

5. The system of claim 1, wherein the medical device defines a longitudinal axis, each of the at least one array arm including a first portion and a second portion, the first portion being in a plane that is substantially orthogonal to the longitudinal axis of the device.

6. The system of claim 1, wherein each of the mapping elements records monophasic action potentials, such that at least one of depolarization timing, repolarization timing, action potential morphology, and action potential duration is unambiguously determined.

7. The system of claim 1, wherein each mapping element has a curved surface.

8. The system of claim 1, wherein each of the plurality of treatment elements includes a first portion that is at least partially wrapped around one of the at least one array arm and a second portion that extends a distance from the at least one array arm.

9. The system of claim 8, wherein the mapping element protrudes from the first portion of the treatment element from which the mapping element protrudes.

10. A medical system comprising: a medical device defining a distal end including: at least one array arm; and a plurality of treatment elements coupled to the at least one array arm, each of the plurality of treatment elements having: a mapping element that protrudes from the treatment element and has a curved surface; a layer of insulation between the treatment element and the corresponding mapping element; a first portion that is at wrapped around at least a portion of the at least one array arm, the mapping element protruding from the first portion; and a second portion that extends a distance from the first portion; a control unit in communication with the medical device, the control unit being configured to deliver electroporation energy to the plurality of electroporation treatment elements and being programmed to: assess a morphology of an electrical conduction of interest within cardiac tissue based on monophasic action potential signals received from the mapping elements; assess a directionality of the electrical conduction of interest based on signals received from the mapping elements; identify a source of the electrical conduction of interest based on the morphology and directionality of the electrical conduction of interest; determine and communicate to a user one or more optimal treatment sites; and disrupt the electrical conduction of interest by activating the plurality of treatment elements in at least one of the one or more optimal treatment sites, activating the plurality of treatment elements including delivering electroporation energy from the control unit to the plurality of electroporation treatment.

* * * * *